United States Patent [19]

Fox et al.

[11] Patent Number: 4,885,407

[45] Date of Patent: Dec. 5, 1989

[54] METHOD FOR RECOVERING A DIHYDRIC PHENOL FROM A SCRAP POLYESTER

[75] Inventors: Daniel W. Fox, Pittsfield; Edward N. Peters, Lenox, both of Mass.

[73] Assignee: General Electric Company, Mt. Vernon, Ind.

[21] Appl. No.: 217,026

[22] Filed: Jul. 11, 1988

[51] Int. Cl.$^4$ .................... C07C 39/16; C07C 37/68
[52] U.S. Cl. .................................................. 568/724
[58] Field of Search ........................................ 568/724

Primary Examiner—Werren B. Lone
Attorney, Agent, or Firm—Martin B. Barancik

[57] ABSTRACT

A method for recovering a dihydric phenol from scrap polyester which comprises a. contacting an aromatic polyester selected from the group consisting of polycarbonate, copolyestercarbonate and a polyarylate with
  (1) an aqueous ammoniacal solution of sufficient strength of sever the ester bonds of the aromatic polyester and
  (2) an alkylchloride in which the polyester is at least partially soluble,
b. forming two mobile liquid phases, the top phase being aqueous and the bottom phase being the alkyl chloride and containing ammonium dihydric phenolate;
c. separating the top phase from the bottom phase;
d. recovering from the bottom phase the dihydric phenol.

12 Claims, No Drawings

METHOD FOR RECOVERING A DIHYDRIC PHENOL FROM A SCRAP POLYESTER

BACKGROUND OF THE INVENTION

In the past, many natural products were formed into articles and cast aside when their useful lives ended. Many of these articles were prepared from naturally occurring materials such as iron or organically based materials which broke down into their constituent parts and essentially returned to the environment from which they were removed. However with the advent of man-made materials, the problem of dealing with scrap products and materials has increased substantially. Many of these materials were not substantially biodegradable. Of particular interest in the last few years are man-made plastic materials. They are becoming ever more useful in many objects in the consumer area, for example packaging materials, automotive parts and appliances. Clearly a method for recovering these scrap materials and converting them to useful constituent chemicals would be quite beneficial to the public.

A new method has been devised for the recovery of dihydric phenol monomers for reuse from aromatic polyester scrap. The method is convenient, practical, and utilizes well known materials.

SUMMARY OF THE INVENTION

In accordance with the invention there is a method for recovering a dihydric phenol from scrap aromatic polyester which comprises a. contacting an aromatic polyester selected from the group consisting of polycarbonate, copolyestercarbonate and a polyarylate with
 (1) an aqueous ammoniacal solution of sufficient strength to sever the ester bonds of the aromatic polyester;
 (2) an alkylchloride which is at least a partial solvent for the polyester;

b. forming two mobile liquid phases, the top phase being aqueous and the bottom phase being the alkyl chloride and containing ammonium dihydric phenolate;

c. separating the top phase from the bottom phase;

d. recovering from the bottom phase the dihydric phenol.

The preferred dihydric phenol recovered is bisphenol-A. The preferred aromatic polyester is polycarbonate.

DETAILED DESCRIPTION OF THE INVENTION

The term "scrap" as employed in this specification and claims is directed to an aromatic polyester which is abandoned because it is no longer of enough worth, merit, use or effectiveness to retain. Examples of such scrap aromatic polyesters include packaging materials, bottles, any reground material which no longer has an economic use in a further molded object, out of specification materials not readily useful for a further application, or any other material which has outlived its useful life.

Aromatic polyesters useful in the invention include aromatic polycarbonates, copolyestercarbonates, and polyarylates. The aromatic polycarbonate resins suitable for use herein as component (a) may be prepared by reacting a dihydric phenol with a carbonate precursor, such as phosgene, a haloformate or a carbonate ester.

Typically, such carbonate polymers are represented as comprising recurring structural units of the formula:

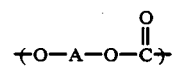

wherein A is a divalent aromatic radical of the dihydric phenol employed in the polymer producing reaction. Preferably, the carbonate polymers used to provide the resinous mixtures of the invention have an intrinsic viscosity (as measured in methylene chloride at 25° C.) ranging from about 0.30 to about 1.20 dl/g. The ammonium salts of the dihydric phenol are preferentially soluble in the alkyl chloride phase. The dihydric phenols which may be employed to provide such aromatic carbonate polymers are mononuclear or polynuclear aromatic compounds, containing as functional groups two hydroxy radicals, each of which is attached directly to a carbon atom of an aromatic nucleus wherein the aromatic nuclei are separated by an alkylene, alkylidene, cycloalkylene or cycloalkylidene group. The aromatic nuclei may be connected by a covalent bond. Typical dihydric phenols are:
2,2-bis-(4-hydroxyphenyl)propane;
2,2-bis-(4-hydroxyphenyl)pentane; biphenol
2,4'-(dihydroxydiphenyl)methane;
bis-(2-hydroxyphenyl)methane;
bis-(4-hydroxyphenyl)methane;
bis-(4-hydroxy-5-nitrophenyl)methane;
1,1-bis(4-hydroxyphenyl)ethane;
3,3-bis(4-hydroxyphenyl)pentane;
2,2-dihydroxydiphenyl;
2,6-dihydroxynaphthalene;
2,2-bis-(3,5-dimethyl-4-hydroxyphenyl)propane;

Schematically, the preferred dihydric phenols are represented by the formula

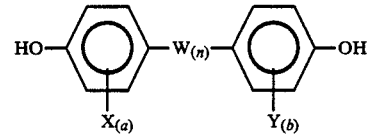

wherein X and Y are the same or different and are chloro, bromo, or alkyl of one to three carbon atoms, inclusive, W is alkylene of two to twelve carbon atoms, inclusive, alkylidene of one to twelve carbon atoms, inclusive, cycloalkylene of from four to eight carbon atoms, inclusive, and cycloalkylidene of four to eight carbon atoms, inclusive;

a and b are the same or different and are 0 or an integer of one to four, n is 0 or 1;

a and b are both preferably zero;

n is preferably one.

The alkylene and alkylidene are normal or branched and preferably have a maximum of eight carbon atoms, inclusive.

Bisphenol-A is preferred.

These aromatic polycarbonates can be manufactured by known processes, such as, for example and as mentioned above, by reacting a dihydric phenol with a carbonate precursor, such as phosgene, in accordance with methods set forth in the above-cited literature and U.S. Pat. Nos. 4,018,750 and 4,123,426, or by transesterification processes such as are disclosed in U.S. Pat. No.

3,153,008 as well as other processes known to those skilled in the art.

It is possible to employ two or more different dihydric phenols or a copolymer of a dihydric phenol with a glycol or with a hydroxy- or acid-terminated polyester or with dibasic acids in the event a carbonate copolymer or interpolymer rather than a homopolymer is desired for use in the preparation of the polycarbonate mixtures of the invention. Branched polycarbonates are also useful, such as are described in U.S. Pat. No. 4,001,184. Also there can be utilized blends of a linear polycarbonate and a branched polycarbonate. Moreover, blends of any of the above materials may be employed in the practice of this invention to provide the aromatic polycarbonate. In any event, the preferred aromatic carbonate polymer for use as component (a) herein is a homopolymer derived from 2,2-bis(4-hydroxyphenyl)propane (bisphenol-A).

The aromatic copolyestercarbonates which can be employed in this invention include those aromatic polymers with ester and carbonate repeating units as those found in U.S. Pat. Nos. 3,169,121; 4,287,787; 4,156,069; 4,260,731 and the like, each incorporated by reference. Of the aforementioned polymers, the polymers utilizing bisphenol-A as the dihydric phenol are preferred. The preferred aromatic acids are isophthalic acid, terephthalic acid or a combination of the two. Methods for preparing the polymers are well known and are described in the references cited above.

Polyarylates are polymers having all ester bonds. They are generally prepared from dihydric phenols and phthalic acids although any aromatic diacid or diphenol can be employed. These polymers and their methods of preparation are well known and are available commercially, for example under the tradename ARDEL from AMOCO. The dihydric phenol preferably employed is bisphenol-A and the aromatic diacid is terephthalic, isophthalic or a combination of the two.

In the past, polycarbonate resin has been rapidly degraded for analytical purposes by contacting the resin with an alcoholic solution of potassium hydroxide or sodium hydroxide in a solvent such as tetrahydrofurane. This caused a rapid cleavage of polycarbonate and the concurrent measurement of the dihydric phenol. In this present invention, the strong hydroxide bases are not employed. Rather an ammoniacal solution is used. Additionally an ether is not used for solubilization. Rather, a traditional alkyl chloride such as 1,2-dichloroethylene, chloroform, methylene chloride, or other chlorinated alkyls such as isopropyl chloride is employed as the solubilization material. Methylene chloride is preferred.

Generally, it is expected that the salts of a dihydric phenol would be soluble in an aqueous phase as opposed to an organic phase. This is the rationale and the driving means of the interfacial preparation of polycarbonate and copolyestercarbonate wherein the sodium salt of bisphenol-A is soluble in the aqueous sodium hydroxide while the phosgene and resultant polycarbonate resin is soluble in the methylene chloride stage. However in this invention, when the ammonium dihydric phenolate is formed after contacting the polycarbonate resin in the mixture of alkyl chloride and ammonium hydroxide, the resultant ammonium dihydric phenolate salt is found to be preferentially soluble in the alkyl chloride phase. Such solubility up to very large concentrations, of at least 70 wt. % of the alkyl chloride phase, brings about a significant separation of the dihydric phenol from the other monomer units of the molecule whether it be solely the carbonate, the carbonate and aromatic acid, or the aromatic acid per se as found in the polyarylate thereby meeting the requirements of this invention. From this point onward, it is a relatively easy task to separate the alkyl chloride phase from the aqueous phase and recover the dihydric phenol from the organic phase. Various methods of recovering the dihydric phenol can be employed. The alkyl chloride can simply be heated to its boiling point wherein it and the ammonia are removed, leaving the dihydric phenol. The ammonia can be recycled if desired. Alternatively, the alkyl chloride is added to a hot solvent which boils at a higher temperature than the alkyl chloride and in which bis-phenol-A is insoluble at a lower temperature. Examples of such solvents include toluene, xylene, benzene and chlorobenzene. The heat of the hot solvent distills off the low boiling alkyl chloride and also the ammonia present in the salt form of the phenolate. Therefore as the solvent cools, the substantially purified dihydric phenol crystallizes therefrom.

The strength of the ammonium hydroxide is relatively important. The strength of the ammonium hydroxide should be sufficient to cleave the aromatic polyester bonds in a relatively short period of time and in a substantially complete manner. Generally, concentrated ammonium hydroxide, that material which has a molarity of about 18, can be effectively and readily employed. However, less concentrated ammonium hydroxide can be employed, for example, down to a molarity of about 9. When using a weaker solution of ammonium hydroxide, the contact time with the aromatic polyester may be longer so as to ensure cleavage of the carbonate bonds. The ammonium hydroxide cleaves the aromatic polyester bond and forms salts of the dihydric phenol, salts and potentially amides as well. It forms urea with the monomer units of the polymer. Therefore, preferably there should be substantially more than four times, in mole quantities, ammonium hydroxide present contacting the polyester than moles of dihydric phenol present in the polyester. A suitable molar range of ammonium hydroxide to dihydric phenol would be from about 4.1 to about 20 times, preferably about 5 to 15. Although not wishing to be governed by this particular theory of the invention, it is believed that this additional ammonium hydroxide brings about significant solubility of the dihydric phenol phenolate salts in the organic alkyl chloride phase. The progress of the severing of the polymer can be monitored by measuring the presence of carbonate or ester bonds, usually by spectrography. When no more carbonate or ester bonds are present, the dihydric phenol is completely liberated. The aqueous phase contains the remainder of the severed aromatic polyester. When aromatic polycarbonate is employed, urea is found in the aqueous phase. When a copolyestercarbonate is cleaved, urea and the aromatic acid ammonium salt are found in the aqueous phase. Finally when a polyarylate is cleaved, the acid ammonium salts and/or amide of the acid are found in the aqueous phase.

The organic phase has also been found to be significant. It is only a relatively small number of alkyl chloride compounds which are effective in this separation scheme. For example, an aromatic chlorine compound such as chlorobenzene is ineffective as a solvent in this recovery system. A nonchlorinated aromatic solvent such as toluene was also found to be nonoperative in this system. Clearly when using the alkyl chloride solvent, there should be a sufficient amount of solvent to place at least a portion of the aromatic polyester initially into solution and thereafter a sufficient amount of solvent for the liberated dihydric phenol. Generally speaking, the range from about 50 to about 500 wt. % of the aromatic polyester resin is a sufficient quantity for the alkyl chloride solvent. A preferred range is from about 100 to about 300. Above the outer limit there is no practical advantage. Below the lower range, there generally is insufficient or too slow a solubilization of the aromatic polyester.

It should be noted that the form of the dihydric phenol in the alkylchloride phase is referred to as an ammonium salt. The analysis has not been done and the exact form of the dihydric phenol is not known. It is believed to be an ammonium salt; however it may be an ammonium bisphenol complex of some nature or a mixture of the ammonium salt and complex to varying degrees.

It should be noted that the method of recovering the dihydric phenol from the scrap aromatic polyester is not limited to the scrap aromatic polyesters per se. Rather blends of the aromatic polyesters with other polymers can also be employed. Examples of such blends include polycarbonates with polyesters such as polyethyleneterephthalate or polystyrenes. Particularly easily separable are the aromatic polyester compositions with solid additives therein. Examples of such additives include pigments, and reinforcing materials such as glass or carbon fibers. The solid materials can be removed anywhere in the processing sequence but should be removed before the isolation of the solid dihydric phenol occurs.

The actual separation of the dihydric phenol from the other monomer(s) is accomplished with a minimum contamination of the alkyl chloride phase. Very little dihydric phenol is found in the aqueous phase.

Below are examples of the invention. These examples are intended to illustrate and not to narrow the inventive concept.

EXAMPLE 1

Sixty grams (0.236 moles) LEXAN® 101 polycarbonate resin, bisphenol-A polycarbonate with an intrinsic viscosity at 25° C. in methylene chloride, dl/g, of 0.53 to 0.55, 400 ml (5.91 moles) was dissolved in a combination of 400 ml (5.91 moles) ammonium hydroxide, 28% ammonia, density equals 0.898 and methylene chloride, 300 mls. After stirring for two hours, the polycarbonate was in solution. Infared analysis of the methylene chloride phase indicated a strong absorbence of carbonate carbonyl group. The mixture was stirred overnight (18 hours). The analysis of the methylene chloride phase showed no carbonate bond. The layers were separated.

Upon evaporation the aqueous layer had about 14.4 gms. of urea and 1.6 gms. of bisphenol-A. The methylene chloride phase was washed with 200 ml water and separated. Bisphenol-A started to precipitate from solution. The precipitate was isolated by filtration to yield 40 gms. bisphenol-A. The methylene chloride was evaporated to give 4 gms. of bisphenol-A. A total of 45.6 gms. of bisphenol-A was recovered, a yield of 6% based upon bisphenol-A in the starting polycarbonate resin.

EXAMPLE 2

The procedure of Example 1 was followed except that 350 ml of methylene chloride was used and the mixture was stirred 24 hours. The aqueous and methylene chloride layer were then separated and evaporated to dryness. The methylene chloride layer yielded 49.1 gms bisphenol-A. The aqueous layer yielded 1.5 gms bisphenol-A. The total of 50.6 gms bisphenol-A was a 95% yield.

EXAMPLE 3

Following the procedure of Example 1 and utilizing the same quantities of materials, the bisphenol polycarbonate, ammonium hydroxide and methylene chloride were stirred in a one liter resin kettle with a mechanical stirrer operating at 400 RPM. After two hours spectroscopic evidence demonstrated that >99% of the bisphenol-A was in its monomeric form. After 24 hours, the bisphenol-A and urea were recovered as in Example 2. The methylene chloride layer contained 52 g of bisphenol-A. The aqueous layer contained 13 g urea and 0.6 g of bisphenol-A. The yield of bisphenol-A based on bisphenol-A in the polycarbonate was 98.5%.

EXAMPLE 4

Following the procedure of Example 3 but utilizing only 200 ml (2.95 moles) of the ammonium hydride, after three (3) reaction hours, the percentage of bisphenol-A in its monomeric form was 96.5%. After 24 hours, the bisphenol-A and urea were recovered. The methylene chloride layer contained 51 g of bisphenol-A. The aqueous layer contained 13.5 g urea and 0.7 g of bisphenol-A. The yield of bisphenol-A was 96.8%.

EXAMPLE 5

Following the procedure of Example 3 but utilizing only 100 ml (1.4 moles) of the ammonium hydroxide, after four (4) reaction hours the percentage of bisphenol-A in its monomeric form was 84.1%. After 24 hours, 98.4% of the bisphenol-A was in its monomeric form. At this time, the bisphenol-A and urea were recovered. The methylene chloride layer contained 50 g of bisphenol-A. The aqueous layer contained 13 g urea and 0.4 g of bisphenol-A. The yield of bisphenol-A was 94.9%.

Examples 3, 4 and 5 show the effect of decreased quantities of ammonium hydroxide on the rate of reaction and the recovery of bisphenol-A.

EXAMPLE 6

Following the procedure of Example 1 and utilizing only 77 ml of the ammonium hydroxide (1.13 moles), the mixture was stirred in the 1 liter resin kettle at 400 rpms for 24 hours. The methylene chloride layer was separated and evaporated to dryness. The methylene chloride layer yielded 46 gms of bisphenol-A or a yield of 86%.

This example shows the yield when a 20% excess of ammonium hydroxide based on a molar basis is employed.

EXAMPLE 7

Following the procedure of Example 1 except that only 64 ml of ammonium hydroxide (0.944 moles) was used, after 24 hours of stirring the reagents at 400 rpm, the methylene chloride layer was analyzed for bisphenol-A following evaporation. 37 gms of bisphenol-A were present. A yield of 80.2% was obtained.

This example shows the yield when the exact stoichiometric ratio of ammonium hydroxide to bisphenol-A units is used. It should be noted that with decreasing ammonium hydroxide, there is decreasing yield of bisphenol-A.

EXAMPLE 8

Following the procedure of Example 1 except for the fact that 200 ml of ammonium hydroxide (2.95 moles) and 150 ml of methylene chloride were employed as the reagents, a 1 liter resin kettle was stirred at 400 rpm for 24 hours. The methylene chloride and aqueous layers were separated and evaporated to dryness. 47.5 gms of bisphenol-A were found in the methylene chloride layer. 0.48 gms of bisphenol-A were found in the aqueous layer. The combination of 47.9 gms bisphenol-A provided a yield of 92.6% of theoretical.

This example shows that the addition of more ammonium hydroxide and the decrease of solvent provided a more concentrated solution and increasingly better yields of bisphenol-A.

EXAMPLE 9

Following the procedure of Example 1 except that 200 ml of ammonium hydroxide (2.95 moles) and 60 ml of methylene chloride were used as the solvent. Over a time of 24 hours, the 1 liter resin kettle was stirred at 400 rpm. The methylene chloride layer was separated from the water layer, evaporated to dryness and analyzed for bisphenol-A. The methylene chloride layer had 49.5 gms bisphenol-A; a yield of 95.8% of theoretical.

This example was essentially the same as the prior example except that an even more concentrated solution was used showing the increasing yield of bisphenol-A when there is a smaller quantity of alkyl chloride solvent.

EXAMPLE 10

Following the procedure of Example 1 but utilizing 60 gms of bisphenol-A polycarbonate which was 20% glass filled, that is 48 gms of bisphenol-A polycarbonate present, 200 ml of ammonium hydroxide and 200 ml of methylene chloride were also added to a 1 liter resin kettle equipped with a mechanical stirrer. The reagents were stirred at 400 rpm. After 7 hours the mixture was filtered through a sintered glass funnel in order to remove the glass. The layers of the filtrate were separated and solvent evaporated. In the methylene chloride layer were 38 gms of bisphenol-A. A yield of 93% was obtained.

EXAMPLE 11

Following the procedures of Example 1 and 2 but utilizing a copolyestercarbonate having about 80 mole % ester content and prepared from iso and terephthaloyl chlorides, similar results should be obtained.

EXAMPLE 12

Following the procedures of Examples 1 and 2 but utilizing a 50% isophthalate terephthalate concentration polyarylate prepared from bisphenol-A, similar results should be obtained for recovery of the bisphenol-A.

EXAMPLE 13

60 gms of a copolymer polycarbonate prepared from 60 mole percent bis-(3,5-dimethyl-4-hydroxyphenyl) sulfone and 40 mole percent bisphenol-A was reacted with 200 ml of ammonium hydroxide as used in Example 1 and 200 ml of methylene chloride as solvent. The reaction was carried out in a 1 liter resin kettle equipped with a mechanical stirrer. The reagents were stirred 400 rpm for 24 hours. The methylene chloride and aqueous layers were separated and evaporated to dryness. In the methylene chloride were 17.6 gms of bisphenol-A and 3.8 gms of the sulfone dihydric phenol. In the aqueous layer were 0.4 gms bisphenol-A and 13.7 gms of the sulfone dihydric phenol.

This example indicates that a copolymer utilizing a different hetero atom such as a sulfur group will give somewhat different partition coefficients between the aqueous and organic phase in comparison to the bisphenol-A dihydric phenol. Sulfone containing dihydric phenols give unsatisfactory yields utilizing the methods of this invention.

EXAMPLE 14

Following the procedures of Examples 1 and 2, other dihydric phenol polycarbonates are employed, for example those included in the list noted earlier in the specification. Similar results with respect to Examples 1 and 2 should be obtained.

EXAMPLE 15

Bisphenol-A recovered from Examples 1 and 2 was then utilized to prepare bisphenol-A polycarbonate. Forty-five (45) grams of bisphenol-A was added to 300 ml of methylene chloride and 230 ml of water which is maintained at a pH of about 10.5 to 11.5 during the course of the reaction. Phosgene at a rate of 0.5 gms. per minute was added for a total of 45 minutes. Also present in the reaction vessel initially was paratertiarybutyl phenol at a quantity of 0.74 grams (2.5 mole percent based on the bisphenol-A). The stirring of the reactor contents was maintained for several minutes past the addition of the phosgene. The methylene chloride phase was separated, washed with a 5% hydrochloric acid solution and then washed a further three times with water. The polymer was isolated by precipitation in hot water, filtered and dried.

Forty-eight (48) grams of bisphenol-A polycarbonate was isolated with an intrinsic viscosity of 0.59 dl/g. A Tg of 151° C. was obtained by DSC. This shows that bisphenol-A recovered from scrap polycarbonate can be employed to prepare bisphenol-A polycarbonate once more.

Following the procedures of this invention, an excellent recovery of dihydric phenols from aromatic polyesters, particularly bisphenol-A from polycarbonate can be obtained in a relatively quick and facile manner.

What is claimed is:

1. A method for recovering a dihydric phenol from scrap polyester which comprises
   a. contacting an aromatic polyester selected from the group consisting of polycarbonate, copolyestercarbonate and a polyarylate with
      (1) an aqueous ammoniacal solution of sufficient strength to sever the ester bonds of the aromatic polyester, and
      (2) an alkylchloride in which the polyester is at least partly soluble,
   b. forming two mobile liquid phases, the top phase being aqueous and the bottom phase being the alkyl chloride and containing ammonium dihydric phenolate;
   c. separating the top phase from the bottom phase;
   d. recovering from the bottom phase the dihydric phenol.
2. The method in accordance with claim 1 wherein the dihydric phenol is bisphenol-A.

3. The method in accordance with claim 1 wherein the alkyl chloride is methylene chloride.

4. The method in accordance with claim 1 wherein ammoniacal solution is ammonium hydroxide.

5. The method in accordance with claim 1 wherein the polyester is polycarbonate.

6. The method in accordance with claim 1 wherein the polyester is copolyestercarbonate.

7. The method in accordance with claim 1 wherein the polyester is polyarylate.

8. The method in accordance with claim 5 wherein the dihydric phenol is bisphenol-A.

9. The method in accordance with claim 6 wherein the dihydric phenol is bisphenol-A.

10. The method in accordance with claim 7 wherein the dihydric phenol is bisphenol-A.

11. The method in accordance with claim 5 wherein the alkyl chloride is methylene chloride.

12. The method in accordance with claim 11 wherein the ammoniacal solution is ammonium hydroxide.

* * * * *

UNITED STATES PATENT AND TRADEMARK OFFICE
CERTIFICATE OF CORRECTION

PATENT NO. : 4,885,407

DATED : December 5, 1989

INVENTOR(S) : Daniel W. Fox
Edward N. Peters

It is certified that error appears in the above-identified patent and that said Letters Patent is hereby corrected as shown below:

On the first page
Under Abstract
Line 8
Delete the first "of" and add "to"

Signed and Sealed this

Sixth Day of November, 1990

Attest:

HARRY F. MANBECK, JR.

Attesting Officer

Commissioner of Patents and Trademarks